United States Patent [19]

Krämer et al.

[11] Patent Number: 5,530,016

[45] Date of Patent: Jun. 25, 1996

[54] SUBSTITUTED 2,4-IMIDAZOLIDINEDIONES

[75] Inventors: Thomas Krämer, Wuppertal; Rudolf Hanko, Essen; Jürgen Dressel, Radevormwald; Peter Fey, Wuppertal; Walter Hübsch, Wuppertal; Ulrich Müller, Wuppertal; Matthias Müller-Gliemann, Solingen; Martin Beuck, Erkrath; Hilmar Bischoff, Wuppertal; Stefan Wohlfeil, Hilden; Dirk Denzer, Wuppertal; Stanislav Kazda, Wuppertal; Johannes-Peter Stasch, Solingen; Andreas Knorr, Erkrath; Siegfried Zaiss, Wuppertal, all of Germany

[73] Assignee: Bayer Aktiengesellschaft, Leverkusen, Germany

[21] Appl. No.: 245,328

[22] Filed: May 18, 1994

[30] Foreign Application Priority Data

May 25, 1993 [DE] Germany ............... 43 17 321.7

[51] Int. Cl.⁶ ............... A61K 31/41; C07D 257/00
[52] U.S. Cl. ............... 514/381; 548/253
[58] Field of Search ............... 548/253; 514/381

[56] References Cited

FOREIGN PATENT DOCUMENTS 0324377 7/1989 European Pat. Off. .
0412594 2/1991 European Pat. Off. .
92/07834 5/1992 WIPO .

OTHER PUBLICATIONS

CA 85: 194264 1976.
CA 74: 75896 1970.
JP 52/100 469 (Feb. 20, 1976).
JP 52/140 470 (May 11, 1976).
The Journal of Cell Biology, vol. 50, 1971, pp. 172–186.
Chemical Abstracts, vol. 88, No. 7, 13 Feb. 1978, abstract No. 50859z, p. 549.

*Primary Examiner*—Sharon Gibson
*Assistant Examiner*—Catherine Scalzo
*Attorney, Agent, or Firm*—Sprung Horn Kramer & Woods

[57] ABSTRACT

Novel substituted 2,4-imidazolidinediones are prepared either by reaction of α-aminocarboxylic acid derivatives with appropriately substituted biphenylmethyl halides and subsequent cyclization with isocyanates or by reaction of N-benzyl-substituted α-aminocarboxylic acid derivatives with tetrazolylphenylboronic acids or by reaction of sulphonyl-substituted benzyl halides with α-aminocarboxylic acid derivatives and subsequent cyclization with isocyanates. The compounds according to the invention can be employed as active compounds in medicaments, preferably for the treatment of arterial hypertension and arteriosclerosis.

11 Claims, No Drawings

SUBSTITUTED 2,4-IMIDAZOLIDINEDIONES

The present invention relates to substituted 2,4-imidazolidinediones, to processes for their preparation and to their use in medicaments, in particular as hypotensive and anti-atherosclerotic agents.

It is known that renin, a proteolytic enzyme, eliminates the decapeptide angiotensin I from angiotensinogen in vivo, and the angiotensin I is in turn degraded in the lungs, the kidneys or other tissues to the hypertensive octapeptide angiotensin II. The various effects of angiotensin II, such as, for example, vasoconstriction, $Na^+$ retention in the kidney, aldosterone release in the adrenal gland and an increase in tone of the sympathetic nervous system act synergistically in the sense of a blood pressure increase.

Moreover, angiotensin II has the property of promoting the growth and the replication of cells such as, for example, heart muscle cells and smooth muscle cells, these growing and proliferating in an increased manner in various disease states (for example hypertension, atherosclerosis and cardiac insufficiency).

A possible starting point for intervention in the renin-angiotensin system (RAS) is, in addition to the inhibition of renin activity, the inhibition of the activity of angiotensin-converting enzyme (ACE) and the blockade of angiotensin II receptors.

Phenylmethyl- and biphenylmethyl-hydantoin derivatives have already been disclosed in the publications JP 52/100 and JP 52/140 470.

The present invention relates to substituted 2,4-imidazolidinediones of the general formula (I)

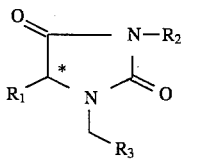

(I)

in which
  $R^1$ represents straight-chain or branched alkyl having up to 8 carbon atoms,
  $R^2$ represents cycloalkyl having 3 to 8 carbon atoms, or represents straight-chain or branched alkyl having up to 8 carbon atoms, which is optionally substituted by phenyl, or
  represents a group of the formula $-CH_2-CO_2R^4$,
  in which
    $R^4$ denotes hydrogen or straight-chain or branched alkyl having up to 8 carbon atoms,
  or
    represents phenyl which is optionally substituted by halogen, cyano, trifluoromethyl or trifluoromethoxy,
  $R^3$ represents a radical of the formula

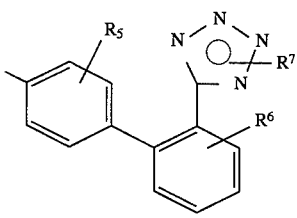

or

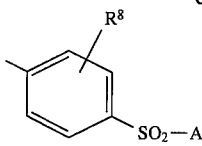

in which
  $R^5$, $R^6$ and $R^8$ are identical or different and denote hydrogen, halogen, cyano, nitro or straight-chain or branched alkyl or alkoxy in each case having up to 6 carbon atoms,
  $R^7$ denotes hydrogen, straight-chain or branched alkyl having up to 6 carbon atoms or the triphenylmethyl group,
  A denotes a 3- to 8-membered, saturated heterocycle having up to 2 heteroatoms from the group consisting of S, N and O, which is bonded via the nitrogen atom and which is optionally substituted up to 2 times by an identical or different radical of the formula

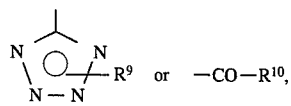

in which
  $R^9$ has the abovementioned meaning of $R^7$ and is identical to or different from this,
  $R^{10}$ denotes hydroxyl or straight-chain or branched alkoxy having up to 6 carbon atoms, or
  denotes a group of the formula $-NR^{11}R^{12}$,
  in which
    $R^{11}$ and $R^{12}$ are identical or different, and denote hydrogen or straight-chain or branched alkyl having up to 6 carbon atoms
and their salts.

The substituted 2,4-imidazolidinediones according to the invention can also be present in the form of their salts. In general, salts with organic or inorganic bases or acids may be mentioned here.

In the context of the present invention, physiologically acceptable salts are preferred. Physiologically acceptable salts of the substituted 2,4-imidazolidinediones can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid, trifluoroacetic acid or benzoic acid.

Physiologically acceptable salts can also be metal or ammonium salts of the compounds according to the invention which have a free carboxyl group. Particularly preferred salts are, for example, sodium, potassium, magnesium or calcium salts and also ammonium salts which are derived from ammonia or organic amines such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms, either as enantiomers or as diastereomers. The invention relates both to the enantiomers or diastereomers and to their respective mixtures. Like the diastereomers, the racemic forms can also be separated in a known manner into the stereoisomerically uniform constituents.

A 3- to 8-membered saturated heterocycle bonded via N, which as heteroatoms can additionally contain up to 2 oxygen, sulphur and/or nitrogen atoms, is in general azetidinyl, piperidyl, morpholinyl, piperazinyl or pyrrolidyl. Preferred 5- and 6-membered rings are those containing an oxygen and/or up to 2 nitrogen atoms, such as, for example azetidinyl, piperidyl, morpholinyl or piperazinyl or pyrrolidinyl. Piperidyl and pyrrolidinyl are particularly preferred.

Preferred compounds of the general formula (I) are those in which $R^1$ represents straight-chain or branched alkyl having up to 6 carbon atoms, $R^2$ represents cyclopropyl, cyclopentyl or cyclohexyl, or represents straight-chain or branched alkyl having up to 6 carbon atoms or benzyl, or represents a radical of the formula —$CH_2CO_2R^4$, in which $R^4$ denotes hydrogen or straight-chain or branched alkyl having up to 6 carbon atoms, or represents phenyl which is optionally substituted by fluorine, chlorine, bromine, cyano, trifluoromethyl or trifluoromethoxy, $R^3$ represents a radical of the formula

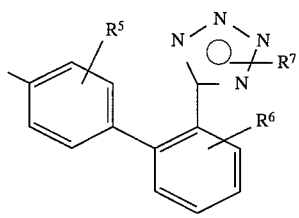

or

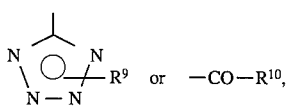

in which $R^5$, $R^6$ and $R^8$ are identical or different and denote hydrogen, fluorine, chlorine, bromine or straight-chain or branched alkyl having up to 4 carbon atoms, $R^7$ denotes hydrogen, straight-chain or branched alkyl having up to 4 carbon atoms or the triphenylmethyl group, A denotes an azetidinyl, piperidyl, pyrrolidinyl or morpholinyl bonded via the nitrogen atom, each of which is optionally substituted by a radical of the formula

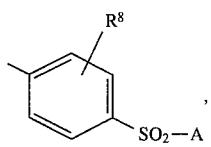

in which $R^9$ has the abovementioned meaning of $R^7$ and is identical to or different from this, $R^{10}$ denotes hydroxyl or straight-chain or branched alkoxy having up to 4 carbon atoms, or denotes a group of the formula —$NR^{11}R^{12}$, in which $R^{11}$ and $R^{12}$ are identical or different and denote hydrogen or straight-chain or branched alkyl having up to 4 carbon atoms, and their salts.

Particularly preferred compounds of the general formula (I) are those in which $R^1$ represents straight-chain or branched alkyl having up to 5 carbon atoms, $R^2$ represents cyclopropyl, cyclopentyl or cyclohexyl, or represents straight-chain or branched alkyl having up to 5 carbon atoms or benzyl, or represents a radical of the formula —$CH_2CO_2R^4$, in which $R^4$ denotes hydrogen or straight-chain or branched alkyl having up to 4 carbon atoms or represents phenyl which is optionally substituted by fluorine, chlorine, bromine or trifluoromethyl, $R^3$ represents a radical of the formula

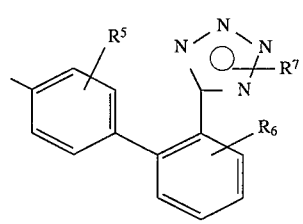

or

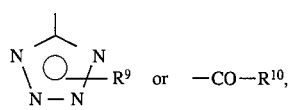

in which $R^5$, $R^6$ and $R^8$ are identical or different and denote hydrogen, fluorine, chlorine or bromine, $R^7$ denotes hydrogen, methyl, ethyl, propyl, isopropyl or the triphenylmethyl group, A denotes azetidinyl, piperidyl or pyrrolidinyl bonded via a nitrogen atom, each of which is optionally substituted by a radical of the formula

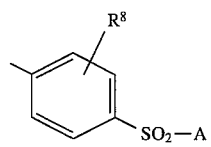

in which $R^9$ has the abovementioned meaning of $R^7$ and is identical to or different from this, $R^{10}$ denotes hydroxyl or straight-chain or branched alkoxy having up to 3 carbon atoms, or denotes a group of the formula —$NR^{11}R^{12}$, in which $R^{11}$ and $R^{12}$ are identical or different and denote hydrogen or straight-chain or branched alkyl having up to 3 carbon atoms, and their salts.

Processes for the preparation of the compounds of the general formula (I) according to the invention were additionally found, characterized in that (I) in the case where $R^3$ represents a radical of the formula

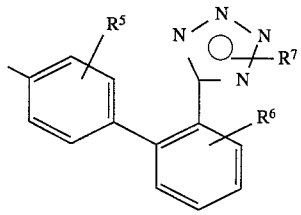

in which $R^5$, $R^6$ and $R^7$ have the abovementioned meaning either

[A] compounds of the general formula (II)

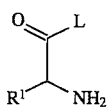 (II)

in which $R^1$ has the abovementioned meaning, and

L represents $C_1$-$C_4$-alkoxy, are first converted by reaction with compounds of the general formula (III)

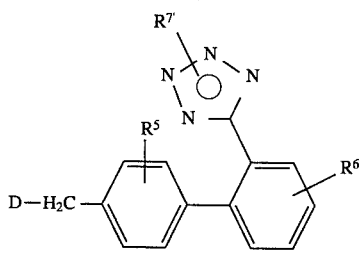 (III)

in which $R^5$ and $R^6$ have the abovementioned meaning,

D represents halogen, preferably bromine and $R^{7'}$ has the abovementioned meaning of $R^7$, but preferably represents the triphenylmethyl group, in inert solvents, in the presence of a base and of a catalyst to the compounds of the general formula (IV)

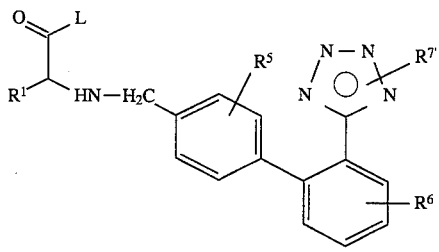 (IV)

in which

L, $R^1$, $R^5$, $R^6$ and $R^{7'}$ have the abovementioned meaning, and in a second step the latter are reacted with compounds of the general formula (V)

$R^2$—N=C=O (V)

in which $R^2$ has the abovementioned meaning, in the presence of acids, or

[B] compounds of the general formula (VI)

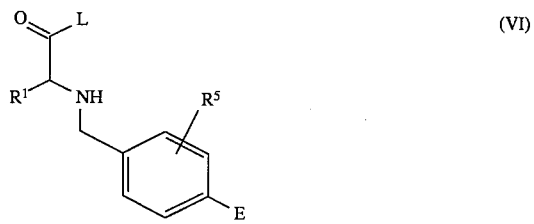 (VI)

in which $R^1$, $R^2$ and L have the abovementioned meaning and

E represents a typical leaving group, such as, for example, bromine, iodine, methane-, toluene-, fluoro- or trifluoromethanesulphonyloxy, preferably bromine, are reacted with compounds of the general formula (VII)

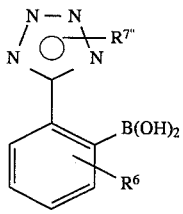 (VII)

in which $R^6$ has the abovementioned meaning and $R^{7''}$ represents hydrogen or the triphenylmethyl group, in inert solvents, in the presence of a base and with metal catalysis, and

[II] in the case where $R^3$ represents the radical of the formula

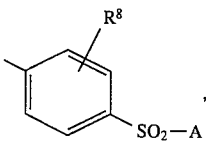

in which $R^8$ and A have the abovementioned meaning, compounds of the general formula (II) are first converted by reaction with compounds of the general formula (VIII)

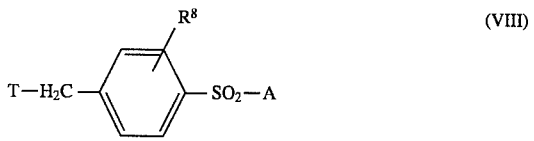 (VIII)

in which

A and $R^8$ have the abovementioned meaning and

T has the abovementioned meaning of D and is identical to or different from this, in inert solvents, in the presence of a base, to the compounds of the general formula (IX)

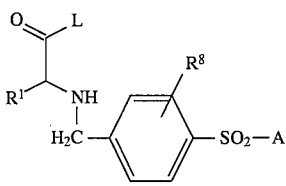

in which

A, L, $R^1$ and $R^8$ have the abovementioned meaning,
and then, as described in [A], the latter are reacted with compounds of the general formula (V),
and then if $R^7/R^9$=a triphenylmethyl group, it is removed with acids in organic solvents and/or water according to customary conditions,
and, if appropriate, in the case of the alkoxy radicals mentioned under the substituents $R^{10}$, converted to the acids by alkaline hydrolysis of the respective esters or derivatized by amidation according to customary methods,
and in the case of the salts, preferably starting from the free tetrazole ($R^7/R^9$=H), reacted with acids or bases,
and, if appropriate, the substituents $R^1$, $R^2$, $R^5$, $R^6$ and $R^8$ are varied according to known methods such as, for example, alkylation, alkaline hydrolysis or amidation, in any process step.

The process according to the invention can be illustrated by way of example by the following reaction scheme:

[A]

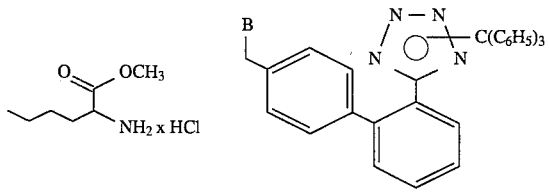

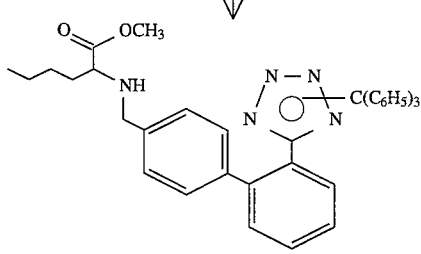

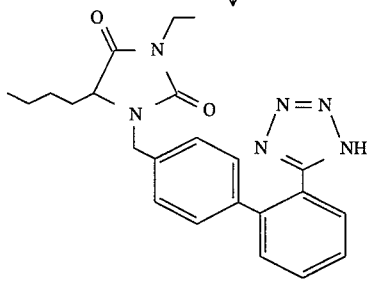

B]

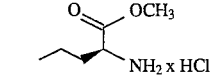 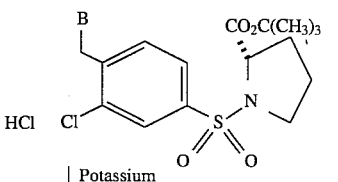

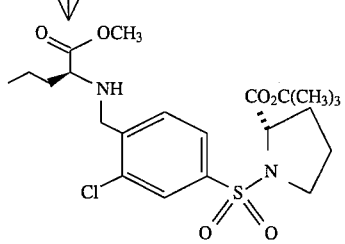

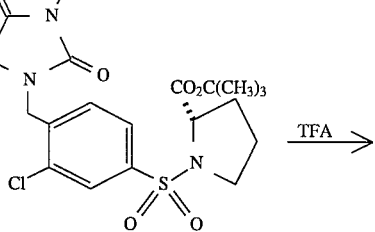

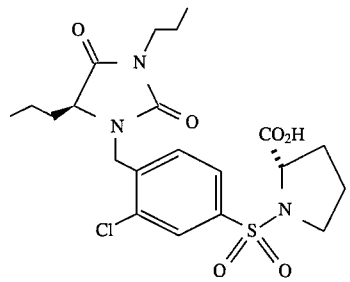

Suitable solvents for processes [I] and [II] are the customary organic solvents which do not change under the reaction conditions. These preferably include ethers such as diethyl ether, dioxane, tetrahydrofuran, glycol dimethyl ether, hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide or dimethoxyethane, hexamethylphosphoramide, acetonitrile, acetone or nitromethane. It is also possible to use mixtures of the solvents mentioned. Tetrahydrofuran, acetone, dichloromethane, dimethylformamide and dimethoxyethane are preferred for processes [I] and [II]. Alcohols such as methanol, ethanol or propanol and/or water are additionally suitable for process [B].

The bases which can be employed for the processes according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate or caesium carbonate, or alkali metal or alkaline earth metal alkoxides or amides such as sodium methoxide or potassium methoxide, sodium ethoxide or potassium ethoxide or potassium tert-butoxide, thallium carbonate or hydroxide, or lithium diisopropylamide (LDA), or organic amines (trialkyl($C_1$–$C_6$)amines) such as triethylamine, or heterocycles such as 1,4-diazabicyclo [2.2.2]octane (DABCO), 1,8-diazabicyclo[5.4.0]undec-7-ene (DBU), pyridine, diaminopyridine, methylpiperidine or morpholine. It is also possible to employ alkali metals, such as sodium or its hydrides such as sodium hydride, as bases. Potassium carbonate, sodium hydride, potassium tert-butoxide and caesium carbonate are preferred for process [A]. Sodium carbonate is preferred for process [B]. Sodium hydride, lithium diisopropylamide (LDA) and DBU are preferred for process [II].

In general, the base is employed in an amount from 0.05 mol to 10 mol, preferably from 1 mol to 2 mol, in each case relative to 1 mol of the compounds of the formulae (III), (VI) and (VIII).

The process according to the invention is in general carried out in a temperature range from −100° C. to +100° C., preferably from 0° C. to 80° C. Process [B] according to the invention is in general carried out under a protective gas atmosphere.

The process according to the invention is in general carried out at normal pressure. However, it is also possible to carry out the process at elevated pressure or at reduced pressure (for example in a range from 0.5 to 5 bar).

The removal of the triphenylmethyl group is carried out using acetic acid or trifluoroacetic acid and water or one of the abovementioned alcohols or using aqueous hydrochloric acid in the presence of acetone or also using alcohols.

The removal is in general carried out in a temperature range from 0° C. to 150° C., preferably from 20° C. to 100° C., and at normal pressure.

Suitable catalysts for process [A] are potassium iodide or sodium iodide, preferably sodium iodide.

Suitable catalysts for process [B] are in general metal complexes of nickel, palladium or platinum, preferably palladium(0) complexes, such as, for example, tetrakistriphenylphosphinepalladium. It is also possible to employ phase-transfer catalysts, such as, for example, tetra-n-butylammoniumbromide or crown ethers.

The catalyst is employed in an amount from 0.005 mol to 0.2 mol, preferably from 0.01 mol to 0.05 mol, relative to 1 mol of the compound of the general formula (VI).

Alkylation is in general carried out using alkylating agents such as, for example, ($C_1$–$C_8$alkyl) halides, sulphonic acid esters or substituted or unsubstituted ($C_1$–$C_8$-dialkyl or ($C_1$–$C_8$)-diaryl sulphonates, preferably methyl iodide or dimethyl sulphate.

Alkylation is in general carried out in one of the abovementioned solvents, preferably in dimethylformamide in a temperature range from 0° C. to +70° C., preferably from 0° C. to +30° C. and at normal pressure.

Suitable bases for hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert-butoxide. Sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide, or dimethyl sulphoxide. Alcohols such as methanol, ethanol, propanol or isopropanol are particularly preferably used. It is also possible to employ mixtures of the solvents mentioned.

The hydrolysis can optionally also be carried out using acids such as, for example, trifluoroacetic acid, acetic acid, hydrochloric acid, hydrobromic acid, methanesulphonic acid, sulphuric acid or perchloric acid, preferably using trifluoroacetic acid.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

The hydrolysis of tert-butyl esters is in general carried out using acids, such as, for example, hydrochloric acid or trifluoroacetic acid, in the presence of one of the abovementioned solvents and/or water or their mixtures, preferably using dioxane or tetrahydrofuran.

The amidation is in general carried out in one of the abovementioned solvents, preferably in tetrahydrofuran or dichloromethane.

The amidation can optionally proceed via the activated stage of the acid halides, which can be prepared from the corresponding acids by reaction with thionyl chloride, phosphorus trichloride, phosphorus pentachloride, phosphorus tribromide or oxalyl chloride.

The amidation is in general carried out in a temperature range from −20° C. to +80° C., preferably from −10° C. to +30° C. and at normal pressure.

Suitable bases for this purpose in addition to the abovementioned bases are preferably triethylamine and/or dimethylaminopyridine, DBU or DABCO.

The base is employed in an amount from 0.5 to 10 mol, preferably from 1 mol to 2 mol, relative to 1 mol of the corresponding acid or ester.

The compounds of the general formulae (II), (III) and (V) are known per se.

The compounds of the general formula (IV) are for the most part new and can be prepared as described above.

The compounds of the General formula (VIII) are for the most part new and can be prepared, for example, in the case where $R^8 \neq$ hydroxyl or ($C_1$–$C_6$)-alkoxy ($R^{8'}$) by reacting compounds of the general formula (X)

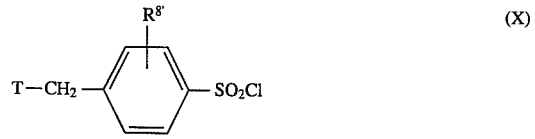

in which $R^{8'}$ and T have the abovementioned meaning,
with compounds of the general formula (XI)

A—H  (XI)

in which A has the abovementioned meaning,
in one of the abovementioned solvents and in the presence of one of the bases described there, preferably in dichloromethane/triethylamine in a temperature range from −10° C. to +120° C., preferably at 0° C.,
and in the case where $R^8$ represents hydroxyl or $(C_1–C_6)$-alkoxy,
starting from carboxyl, hydroxy-disubstituted benzenesulphonyl chlorides, for example 4-carboxy-3-hydroxybenzenesulphochloride, preparing, first by reaction with compounds of the general formula (XI), compounds of the general formula (XII)

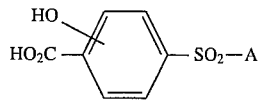
(XII)

in which

A has the abovementioned meaning,
then, by conversion of the carboxyl function to the corresponding benzyl ester and the blocking of the hydroxyl function according to customary methods,
converting to the compounds of the general formula (XIII)

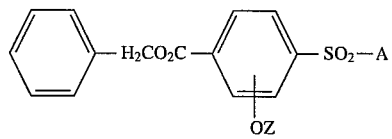
(XIII)

in which

A has the abovementioned meaning
and

Z represents $C_1–C_6$-alkoxy,
in a further step, also according to known methods, preferably using sodium borohydride/LiCl in diglyme, reducing the benzyl ester to the hydroxymethyl function,
and finally brominating with triphenylphosphine dibromide, in one of the abovementioned solvents, preferably dimethylformamide, under a protective gas atmosphere, in a temperature range from 0° C. to room temperature.

The compounds of the general formulae (X) and (XI) are known per se.

The compounds of the general formulae (XII) and (XIII) are for the most part new and can be prepared, for example, as described above.

The compounds of the general formula (VII) where $R^7=H$ are new and can be prepared by first reacting phenyltetrazole and derivatives under a protective gas atmosphere in an inert solvent and in the presence of a base and then adding trimethyl borate and hydrolyzing with acids in a last step.

Suitable solvents for the process are aprotic solvents such as ethers, for example tetrahydrofuran, diethyl ether, toluene, hexane or benzene. Tetrahydrofuran is preferred.

Suitable bases are n-, sec- and tert-butyllithium and phenyllithium. n-Butyllithium is preferred.

The base is employed in an amount from 2 mol to 5 mol, preferably from 2 mol to 3 mol, relative to 1 mol of phenyltetrazole.

Suitable acids are in general mineral acids, such as, for example, hydrochloric acid, $C_1–C_4$-carboxylic acids, such as, for example, acetic acid, or phosphoric acids. Hydrochloric acid is preferred.

The acid is in general employed in an amount from 1 mol to 10 mol, preferably from 1 mol to 3 mol.

The process is in general carried out in a temperature range from −70° C. to +25° C., preferably from −10° C. to 0° C.

The process according to the invention is in general carried out at normal pressure. However, it is also possible to carry out the process at elevated pressure or at reduced pressure (for example in a range from 0.5 to 5 bar).

The compounds of the general formulae (IV) and (IX) are new per se and can be prepared as described above.

The compounds of the general formula (VI) are for the most part new and can be prepared, for example, by reacting compounds of the general formula (II) with compounds of the general formula (XIV)

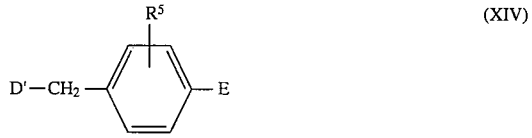
(XIV)

in which $R^5$ and E have the abovementioned meaning
and

D' has the abovementioned meaning of D and is identical to or different from this,
in one of the abovementioned solvents and in the presence of one of the bases described there, preferably in dimethoxyethane and caesium carbonate at room temperature.

The above preparation processes are only given for clarification. The preparation of the compounds of the general formula (I) according to the invention is not restricted to these processes, and any modification of these processes is applicable to the preparation in the same manner.

The substituted 2,4-imidazolidinediones according to the invention show an unforeseeable, useful spectrum of pharmacological action.

The compounds according to the invention have a specific A II-antagonistic action, since they competitively inhibit the binding of angiotensin II to the receptors. They suppress the vasoconstrictor and aldosterone secretion-stimulating effects of angiotensin II. Moreover, they inhibit the proliferation of smooth muscle cells.

They can therefore be employed in medicaments for the treatment of arterial hypertension and atherosclerosis. Moreover, they can be employed for the treatment of coronary heart diseases, cardiac insufficiency, brain function disorders, ischaemic brain diseases, peripheral circulatory disorders, functional disorders of the kidney and adrenal gland, bronchospastic diseases and diseases of the respiratory tract having a vascular cause, sodium retention and oedemas.

The compounds can also be used for the control of glaucoma, diabetic retinopathy and increases in the mobility of the intraocular retinal fluid.

They are also suitable for controlling diseases of the central nervous system such as for example depression, migraine, schizophrenia or anxiety states, brain dysfunctions, strokes, diabetic nephropathy, cardiac dysrhythmias, or for the prophylaxis of coronary heart diseases or restenosis after angioplasty and vascular surgery.

Investigation of the inhibition of the agonist-induced contraction

Rabbits of both sexes are stunned by a blow to the neck and bled out, or in some cases anesthetized with Nembutal (about 60–80 mg/kg i.v.) and sacrificed by opening the thorax. The thorax aorta is taken out, freed from adhering connective tissue, divided into 1.5 mm wide ring segments and individually transferred under an initial loading of about 3.5 g to 10 ml organ baths containing 95% $O_2$/5% $CO_2$-aerated Krebs-Henseleit nutrient solution temperature-controlled at 37° C. of the following composition: 119 mmol/l of NaCl; 2.5 mmol/l of $CaCl_2\times2$ $H_2O$; 1.2 mmol/l of KH$_2$PO$_4$; 10mmol/l of glucose; 4.8 mmol/l of KCl; 1.4 mmol/l of MgSO$_4$×7 H$_2$O and 25 mmol/l of NaHCO$_3$.

The contractions are measured isometrically by Statham UC2 cells by means of bridge amplifiers (ifd Müheim or DSM Aalen) and digitalized and analyzed by means of A/D convertors (System 570, Keithley Munich). Agonist dose response curves (DRC) were plotted hourly. With each DRC, 3 or 4 individual concentrations are applied to the baths at an interval of 4 min. After completion of the DRC and subsequent washing-out cycles (16 times, in each case about 5 sec/min with the abovementioned nutrient solution), a 28-minute resting or incubation phase is added in the course of which the contractions as a rule reach the starting value again.

The height of the 3rd DRC in the normal case is used as a reference quantity for the evaluation of the test substance to be investigated in further passages, which is applied to the baths in the following DRCs in increasing dosage in each case at the start of the incubation time. In this way, each aorta ring is always stimulated for the whole day with the same agonist.

Agonists and their standard concentrations (Administration volume per individual dose=100 µl):

| KCl | 22.7;32.7;42.7;52.7 | mmol/l |
| Noradrenaline | $3 \times 10^{-9}; 3 \times 10^{-8}; 3 \times 10^{-7}$; $3 \times 10^{-6}$ | g/ml |
| Serotonin | $10^{-8}; 10^{-7}; 10^{-6}; 10^{-5}$ | g/ml |
| B-HT 920 | $10^{-7}; 10^{-6}; 10^{-5}$ | g/ml |
| Methoxamine | $10^{-7}; 10^{-6}; 10^{-5}$ | g/ml |
| Angiotensin II | $3 \times 10^{-9}; 10^{-8}; 3 \times 10^{-8}; 10^{-7}$ | g/ml |

To calculate the IC$_{50}$ (concentration at which the substance to be investigated causes a 50% inhibition), the effect is in each case based on the 3rd=submaximal agonist concentration.

The compounds according to the invention inhibit the contraction of the isolated rabbit aorta induced by angiotensin II in a dose-dependent manner. The contraction induced by potassium depolarisation or other agonists was not inhibited or only weakly inhibited at high concentrations.

Blood pressure measurements on the angiotensin II-infused rat

Male Wistar rats (Moellegaard, Copenhagen, Denmark) having a body weight of 300–350 g are anaesthetized with thiopental (100 mg/kg i.p.). After tracheotomy, a catheter for blood pressure measurement is inserted in the femoral artery and a catheter for angiotensin II infusion and a catheter for substance administration are inserted in the femoral veins. After administration of the ganglionic blocker pentolinium (5 mg/kg i.v.), the angiotensin II infusion is started (0.3 µg/kg/min). As soon as the blood pressure values have reached a stable plateau, the test substances are administered either intravenously or orally as a suspension or solution in 0.5% Tylose. The blood pressure changes under the effect of the substance are given in the table as average values ±SEM.

Determination of anti-hypertensive activity in conscious hypertensive rats

The oral antihypertensive activity of the compounds according to the invention was tested on conscious rats having a surgically induced unilateral renal artery stenosis. To do this, the right renal artery was constricted with a silver clip of 0.18 mm internal width.

In this form of hypertension, the plasma renin activity increases in the first six weeks after intervention. The arterial blood pressure of these animals was measured in a bloodless manner at defined time intervals after substance administration using the "tail cuff". The substances to be tested were administered intragastrally ("orally") by stomach tube at various doses suspended in a Tylose suspension. The compounds according to the invention reduce the arterial blood pressure of the hypertensive rats at a clinically relevant dosage.

Additionally, the compounds according to the invention inhibit the specific binding of radioactive angiotensin II in a concentration-dependent manner.

Interaction of the compounds according to the invention with the angiotensin II receptor on membrane fractions of adrenal gland vortex (bovine)

Bovine adrenal gland cortices (AGC) which have been freshly removed and carefully freed from gland medulla are comminuted in sucrose solution (0.32M) with the aid of an Ultra-Turrax (Janke & Kunkel, Staufen i.B.) to give a coarse membrane homogenate and are partially purified to give membrane fractions in two centrifugation steps. The receptor binding investigations are carried out on partially purified membrane fractions of bovine AGC using radioactive angiotensin II in an assay volume of 0.25 ml which, in detail, contains the partially purified membranes (50–80 µg) $^3$H-angiotensin II (3–5 nM), test buffer solution (50 mM tris, pH 7.2), 5 mM MgCl$_2$ and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM tris/HCl, pH 7.4, 5% PEG 6000). The analysis of the raw data was carried out using computer programs to give K$_i$ or IC$_{50}$ values (K$_i$:IC$_{50}$ values corrected for the radioactivity used; IC$_{50}$ values: concentration at which the substance to be investigated causes a 50% inhibition of the specific binding of the radioligand).

Investigation of the inhibition of proliferation of smooth muscle cells by the compounds according to the invention To determine the antiproliferative action of the compounds, smooth muscle cells are used which have been obtained from the aortas of rats or pigs by the media explant technique [R. Ross, J. Cell. Biol. 50, 172, 1971]. The cells are innoculated into suitable culture dishes, as a rule 24-hole plates, and cultured at 37° C. for 2–3 days in medium 199 containing 7.5% FCS and 7.5% NCS, 2 mM L-glutamine and 15 mM HEPES, pH 7.4 in 5% CO$_2$. The cells are then synchronized by withdrawal of serum for 2–3 days and then stimulated into growth with serum or other factors. Test compounds are simultaneously added. After 16–20 hours, 1 µCi of $^3$H-thymidine is added and, after a further 4 hours, the incorporation of this substance into the TCA-precipitatable DNA of the cells is determined. To determine the IC$_{50}$ values, the active compound concentration is calculated which, on sequential dilution of the active compound, causes semi-maximal inhibition of the thymidine incorporation produced by 10% FCS.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proved advantageous on intravenous administration to administer amounts of about 0.001 to 1 mg/kg, preferably about 0.01 to 0.5 mg/kg of body weight to achieve effective results, and on oral administration the dosage is about 0.01 to 20 mg/kg, preferably 0.1 to 10 mg/kg of body weight.

In spite of this, it may be necessary to deviate from the amounts mentioned, namely depending on the body weight or the type of administration route, on individual behaviour towards the medicament, the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into several individual doses over the course of the day.

STARTING COMPOUNDS

Example I

Methyl (rac)-N-{[2'-(N'-triphenylmethyl-tetrazol-5-yl)biphenyl-4-yl]methyl}-2-aminohexanoate

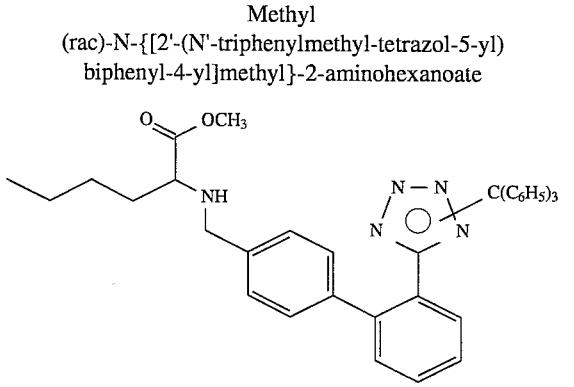

A solution of 4.08 g (22.44 mmol) of methyl (rac)-2-aminohexanoate hydrochloride and 3.15 ml of triethylamine in 50 ml of DME and 25 ml of DMF are treated under argon with 2.43 g (21.69 mmol) of potassium tert-butoxide. After stirring at 20° C. for 30 min, a solution of 15 g (26.93 mmol) of N-triphenylmethyl-5-[2-(4'-bromomethylbiphenyl)]tetrazole in 45 ml of DMF is injected and the mixture is stirred for 36 h. The solvent is then distilled off in vacuo, the residue is taken up with dichloromethane/water, the organic phase is dried over sodium sulphate and after concentration the residue is purified on silica gel using petroleum ether/ethyl acetate (10:1). Yield: 3.27 g (23% of theory) $R_f$: 0.56 (petroleum ether/ethyl acetate= 3:1)

Example II

4-[1-(S)-Methoxycarbonyl-butylamino]methyl-3-chlorobenzenesulphonyl-N-(2-(S)-tert-butoxycarbonyl)piperidinide

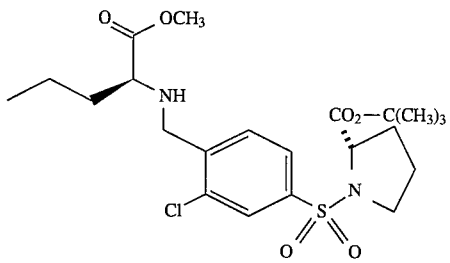

A solution of 1.68 g (10 mmol) of methyl (S)-2-aminovalerate hydrochloride and 1.4 ml of triethylamine in 10 ml of DMF are treated under argon with 1.34 g (11 mmol) of potassium tert-butoxide. After stirring at 20° C. for 45 min, a solution of 4.82 g (11 mmol) of (S)-4-(bromomethyl)-3-chlorobenzenesulphonyl-N-2-(tert-butoxycarbonyl)pyrrolidinide in 30 ml of DMF are injected and the mixture is stirred for 16 h. The solvent is then distilled off in vacuo, the residue is then taken up with dichloromethane/water, the organic phase is dried over sodium sulphate and after concentration the residue is purified on silica gel using petroleum ether/ethyl acetate (10:1). Yield: 1.8 g (37% of theory) $R_f$: 0.76 (petroleum ether/ethyl acetate=2: 1)

Example III

4-[(3S,5-Dipropylimidazolidine-2,4-dion-1-yl]methyl-3-chlorobenzenesulphonyl-N-(2-S-tert-butoxycarbonyl)piperidinide

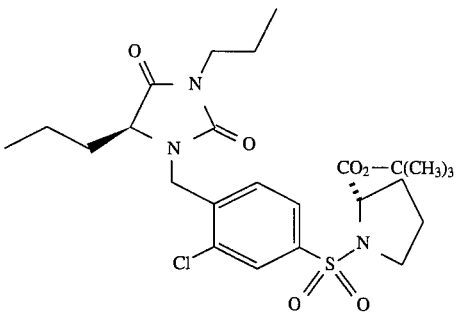

A solution of 489 mg (1.0 mmol) of the compound from Example II and 255 mg (3.0 mmol) of propyl isocyanate in 10 ml of ethyl acetate are heated to reflux for 16 h. 10 ml of ethyl acetate and 5 ml of 5% strength hydrochloric acid are then added and the mixture is washed with 10 ml each of water, satd. sodium hydrogen carbonate and satd. sodium chloride solution. The organic phase is separated off, dried over sodium sulphate and concentrated, and the residue is purified on silica gel using petroleum ether/ethyl acetate (4:1). Yield: 390 mg (68% of theory) $R_f$: 0.63 (petroleum ether/ethyl acetate=2:1)

PREPARATION EXAMPLES

Example 1

(rac)-5-Butyl-3-ethyl-1-{[2'-(tetrazol-5-yl)biphenyl-4-yl]methyl}-imidazolidine-2,4-dione

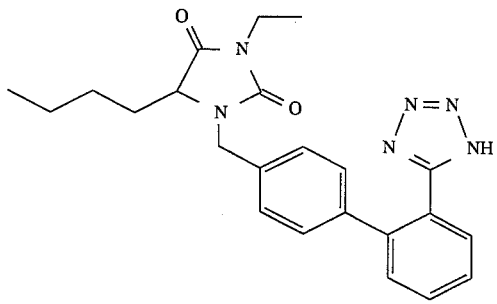

A solution of 300 mg (0.48 mmol) of the compound from Example 1 and 0.115 ml (1.45 mmol) of ethyl isocyanate in 10 ml of ethyl acetate are heated to reflux for 16 h. 2 ml of half-concentrated hydrochloric acid are then added at boiling heat and the heating bath is removed. After 1 h, the cooled solution is diluted with dichloromethane, the phases are separated and the aqueous phase is extracted twice with 20 ml of dichloromethane/ethyl acetate (1:1) each time. The combined organic phases are dried over sodium sulphate, the solvent is removed and the residue is purified on silica gel using toluene/ethyl acetate/glacial acetic acid (35:5:1). Yield: 65.4 mg (32% of theory) $R_f$: 0.37 (toluene/ethyl acetate/glacial acetic acid=20:20:1)

The compounds shown in Tables 1 and 2 are prepared in analogy to the procedure of Example 1:

TABLE 1

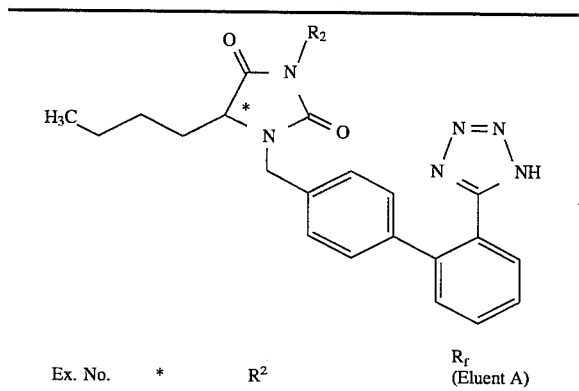

| Ex. No. | * | $R^2$ | $R_f$ (Eluent A) |
|---|---|---|---|
| 2 | (R) | $-C_2H_5$ | 0,37 |
| 3 | (S) | $-C_2H_5$ | 0,37 |
| 4 | (R) | $-(CH_2)_2-CH_3$ | 0,43 |
| 5 | (S) | $-(CH_2)_2-CH_3$ | 0,43 |
| 6 | (rac) | $-(CH_2)_2-CH_3$ | 0,43 |
| 7 | (R) | $-(CH_2)_3-CH_3$ | 0,48 |
| 8 | (S) | $-(CH_2)_3-CH_3$ | 0,48 |
| 9 | (rac) | $-(CH_2)_3-CH_3$ | 0,48 |
| 10 | (R) | $-CH(CH_3)_2$ | 0,57 |
| 11 | (S) | $-CH(CH_3)_2$ | 0,57 |
| 12 | (rac) | $-CH(CH_3)_2$ | 0,57 |
| 13 | (R) | $-C_6H_{11}$ | 0,55 |
| 14 | (S) | $-C_6H_{11}$ | 0,55 |
| 15 | (rac) | $-C_6H_{11}$ | 0,55 |
| 16 | (R) | $-CH_2-C_6H_5$ | 0,53 |
| 17 | (S) | $-CH_2-C_6H_5$ | 0,53 |

TABLE 1-continued

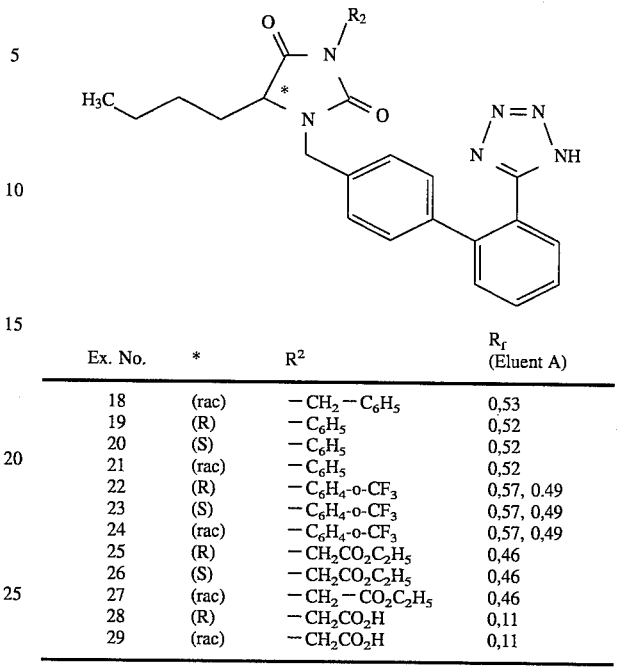

| Ex. No. | * | $R^2$ | $R_f$ (Eluent A) |
|---|---|---|---|
| 18 | (rac) | $-CH_2-C_6H_5$ | 0,53 |
| 19 | (R) | $-C_6H_5$ | 0,52 |
| 20 | (S) | $-C_6H_5$ | 0,52 |
| 21 | (rac) | $-C_6H_5$ | 0,52 |
| 22 | (R) | $-C_6H_4$-o-$CF_3$ | 0,57, 0.49 |
| 23 | (S) | $-C_6H_4$-o-$CF_3$ | 0,57, 0,49 |
| 24 | (rac) | $-C_6H_4$-o-$CF_3$ | 0,57, 0,49 |
| 25 | (R) | $-CH_2CO_2C_2H_5$ | 0,46 |
| 26 | (S) | $-CH_2CO_2C_2H_5$ | 0,46 |
| 27 | (rac) | $-CH_2-CO_2C_2H_5$ | 0,46 |
| 28 | (R) | $-CH_2CO_2H$ | 0,11 |
| 29 | (rac) | $-CH_2CO_2H$ | 0,11 |

Eluent A: Toluene/ethyl acetate/glacial acetic acid (20:20:1)

TABLE 2

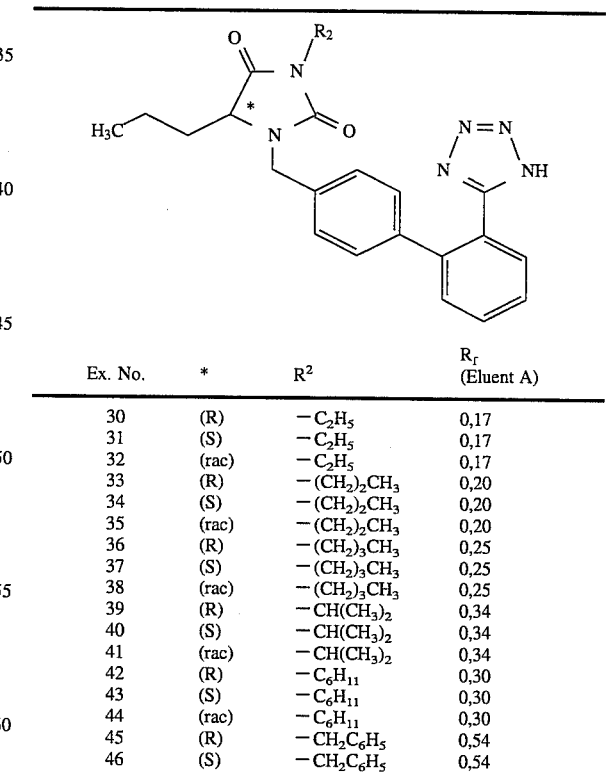

| Ex. No. | * | $R^2$ | $R_f$ (Eluent A) |
|---|---|---|---|
| 30 | (R) | $-C_2H_5$ | 0,17 |
| 31 | (S) | $-C_2H_5$ | 0,17 |
| 32 | (rac) | $-C_2H_5$ | 0,17 |
| 33 | (R) | $-(CH_2)_2CH_3$ | 0,20 |
| 34 | (S) | $-(CH_2)_2CH_3$ | 0,20 |
| 35 | (rac) | $-(CH_2)_2CH_3$ | 0,20 |
| 36 | (R) | $-(CH_2)_3CH_3$ | 0,25 |
| 37 | (S) | $-(CH_2)_3CH_3$ | 0,25 |
| 38 | (rac) | $-(CH_2)_3CH_3$ | 0,25 |
| 39 | (R) | $-CH(CH_3)_2$ | 0,34 |
| 40 | (S) | $-CH(CH_3)_2$ | 0,34 |
| 41 | (rac) | $-CH(CH_3)_2$ | 0,34 |
| 42 | (R) | $-C_6H_{11}$ | 0,30 |
| 43 | (S) | $-C_6H_{11}$ | 0,30 |
| 44 | (rac) | $-C_6H_{11}$ | 0,30 |
| 45 | (R) | $-CH_2C_6H_5$ | 0,54 |
| 46 | (S) | $-CH_2C_6H_5$ | 0,54 |

Eluent A: Toluene/ethyl acetate/glacial acetic acid (30:10:1)

Example 60

4-[(3 S,5-Dipropylimidazolidine-2,4-dione-1-yl]methyl-3-chlorobenzenesulphonyl-N-(2-S-carboxy)piperidinide

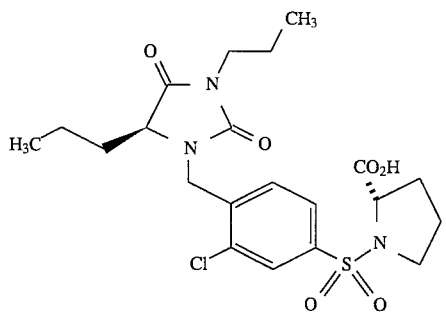

1.45 ml of trifluoroacetic acid are added to a solution of 360 mg (0.66 mmol) of the compound from Example III in 3.5 ml of dichloromethane and the mixture is stirred at 20° C. for 2 h. It is then diluted with 10 ml of dichloromethane, washed with 10 ml of water and the organic phase, after separation, is dried over sodium sulphate and concentrated. The residue is purified on silica gel using toluene/ethyl acetate/glacial acetic acid (35:5:1) Yield: 252 mg (78% of theory) $R_f$: 0.27 (toluene/ethyl acetate/glacial acetic acid 30:10:1)

The compounds shown in Table 3 are prepared in analogy to the procedure of Example 60:

TABLE 3

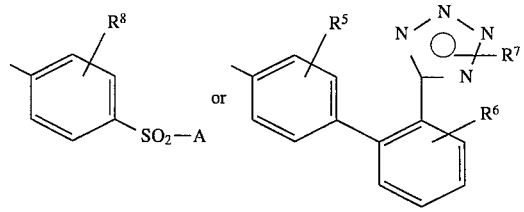

| Ex. No. | * | $R^1$ | $R^2$ | $R_f$ (Eluent A) |
|---|---|---|---|---|
| 61 | (rac) | —(CH$_2$)$_2$CH$_3$ | —C$_2$H$_5$ | 0,25 |
| 62 | (S) | —(CH$_2$)$_2$CH$_3$ | —C$_2$H$_5$ | 0,25 |
| 63 | (S) | —(CH$_2$)$_2$CH$_3$ | —(CH$_2$)$_2$CH$_3$ | 0,27 |
| 64 | (S) | —(CH$_2$)$_2$CH$_3$ | —(CH$_2$)$_3$CH$_3$ | 0,27 |
| 65 | (S) | —(CH$_2$)$_2$CH$_3$ | —CH$_2$CO$_2$C$_2$H$_5$ | 0,25 |
| 66 | (S) | —(CH$_2$)$_3$CH$_3$ | —(CH$_2$)$_2$CH$_3$ | 0,22 |
| 67 | (S) | —(CH$_2$)$_3$CH$_3$ | —(CH$_2$)$_3$CH$_3$ | 0,24 |
| 68 | (S) | —(CH$_2$)$_3$CH$_3$ | —CH$_2$CO$_2$C$_2$H$_5$ | 0,19 |
| 69 | (S) | —CH(CH$_3$)$_2$ | —C$_2$H$_5$ | 0,2 |
| 70 | (S) | —CH(CH$_3$)$_2$ | —(CH$_2$)$_2$CH$_3$ | 0,2 |
| 71 | (S) | —CH(CH$_3$)$_2$ | —(CH$_2$)$_3$CH$_3$ | 0,36 |

Eluent A: Toluene/ethyl acetate/glacial acetic acid (30:10:1)

We claim:

1. A substituted 2,4-imidazolidinedione of the formula

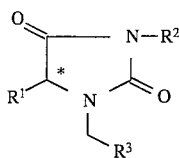

in which $R^1$ represents straight-chain or branched alkyl having up to 8 carbon atoms, $R^2$ represents cycloalkyl having 3 to 8 carbon atoms, or represents straight-chain or branched alkyl having up to 8 carbon atoms, which is optionally substituted by phenyl, or represents a group of the formula —CH$_2$—CO$_2$R$^4$, in which $R^4$ denotes hydrogen or straight-chain or branched alkyl having up to 8 carbon atoms, or represents phenyl which is optionally substituted by halogen, cyano, trifluoromethyl or trifluoromethoxy, $R^3$ represents a radical of the formula

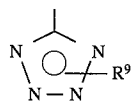

in which $R^5$, $R^6$ and $R^8$ are identical or different and denote hydrogen, halogen, cyano, nitro or straight-chain or branched alkyl or alkoxy in each case having up to 6 carbon atoms, $R^7$ denotes hydrogen, straight-chain or branched alkyl having up to 6 carbon atoms or the triphenylmethyl group, and A denotes a 3- to 8-membered, saturated heterocyclic radical having up to 2 heteroatoms selected from the group consisting of S, O, and N bonded to the SO$_2$, the heterocyclic being substituted up to 2 times by an identical of different radical of the formula $$\begin{array}{c} \text{N} \diagdown \text{O} \diagup \text{N} \\ \text{N} - \text{N} \end{array} R^9$$

in which $R^9$ denotes hydrogen, straight-chain or branched alkyl having up to 6 carbon atoms or the triphenylmethyl group, or a salt thereof.

2. A substituted 2,4-imidazolidinedione according to claim 1 wherein such compound is 5-butyl-3-ethyl-1-{[2'-(tetrazol-5-yl)biphenyl-4-yl]methyl}imidazolidine-2,4-dione of the formula

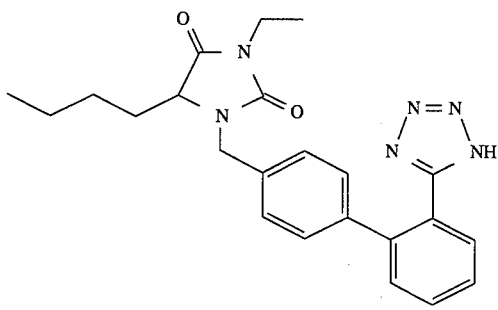

an isomer or salt thereof.

3. A substituted 2,4-imidazolidinedione according to claim 1 wherein such compound is 5-butyl-3-propyl-1-{[2'-(tetrazol-5-yl)biphenyl-4-yl]methyl}imidazoline-2,4-dione of the formula

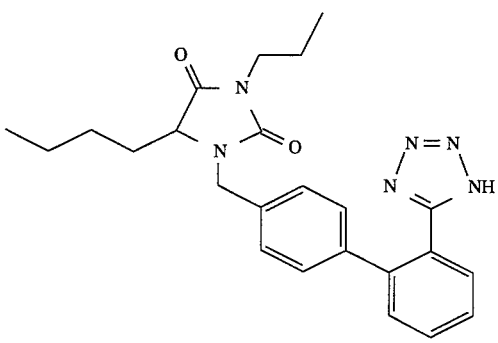

an isomer or salt thereof.

4. A substituted 2,4-imidazolidinedione according to claim 1 wherein such compound is 3,5-butyl-1-{[2'-(tetrazol-5-yl)biphenyl-4-yl]methyl } imidazolidine-2,4-dione of the formula

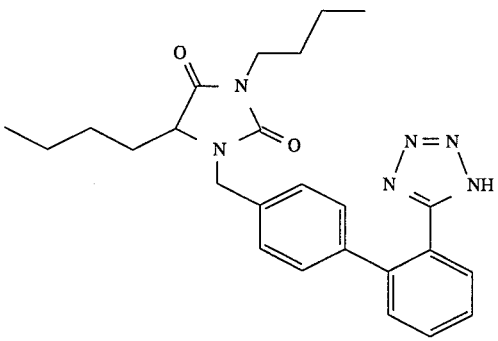

an isomer or salt thereof.

5. A substituted 2,4-imidazolidinedione according to claim 1 wherein such compound is 5-butyl-3-(1-trifluoromethyl-phenyl) -1-{[2'-(tetrazol-5-yl)biphenyl-4-yl] methyl}imidazolidine-2,4-dione of the formula

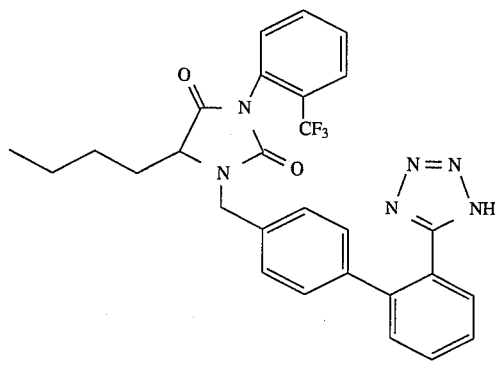

an isomer or salt thereof.

6. A substituted 2,4-imidazolidinedione according to claim 1 wherein such compound is 5-butyl-3-carboxymethyl-1-{[2'-(tetrazol-5-yl)biphenyl -4-yl] methyl}imidazolidine-2,4-dione of the formula

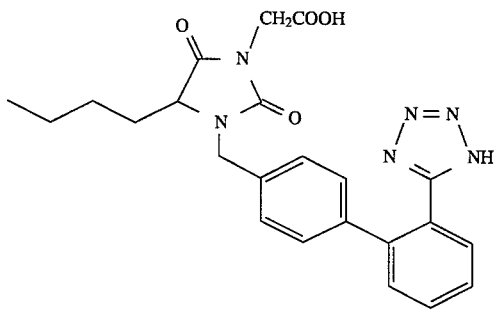

isomer or salt thereof.

7. A substituted 2,4-imidazolidinedione according to claim 1 wherein such compound is 5-butyl-3-isopropyl -1-{[2'-(tetrazol-5-yl)biphenyl-4-yl]methyl}imidazolidine-2,4-dione of the formula

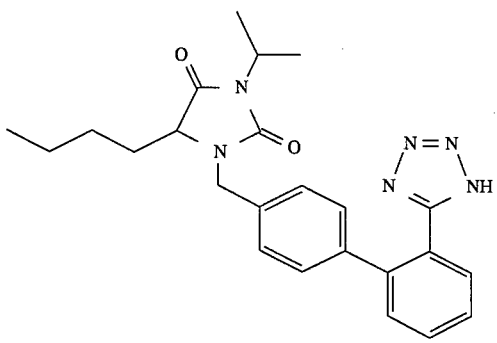

an isomer or salt thereof.

8. A composition for the treatment of arterial hypertension and atherosclerosis comprising an amount effective therefore of a compound or salt thereof according to claim 1 and a pharmacologically acceptable diluent.

9. The method of treating arterial hypertension and atherosclerosis in a patient in need thereof which comprises administering to such patient an amount effective therefore of a compound or salt thereof according to claim 1.

10. A substituted 2,4-imidazolidinedione or salt thereof according to claim 1, $R^1$ represents straight-chain or branched alkyl having up to 6 carbon atoms, $R^2$ represents cyclopropyl, cyclopentyl or cyclohexyl, or represents straight-chain or branched alkyl having up to 6 carbon atoms or benzyl, or represents a radical of the formula —$CH_2CO_2R^4$, in which $R^4$ denotes hydrogen or straight-chain or branched alkyl having up to 6 carbon atoms, or represents phenyl which is optionally substituted by fluorine, chlorine, bromine, cyano, trifluoromethyl or trifluoromethoxy, $R^3$ represents a radical of the formula

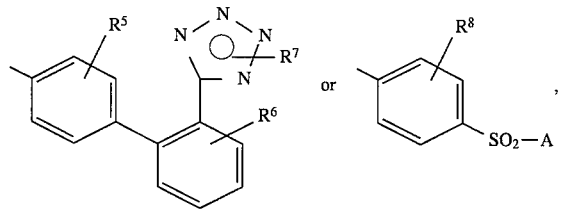

in which $R^2$ represents cyclopropyl, cyclopentyl or cyclohexyl, or represents straight-chain or branched alkyl having up to 6 carbon atoms or benzyl, or represents a radical of the formula —$CH_2CO_2R^4$, in which $R^4$ denotes hydrogen or straight chain or branched alkyl having up to 6 carbon atoms, or represents phenyl which is optionally substituted by fluorine, chlorine, bromine, cyano, trifluoromethyl or trifluoromethoxy, $R^3$ represents a radical of the formula

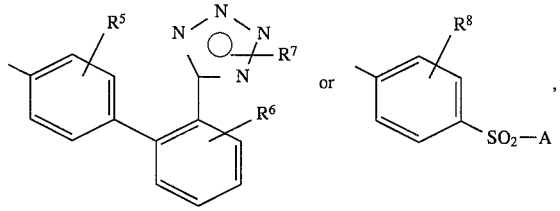

in which $R^5$, $R^6$ and $R^8$ are identical or different and denote hydrogen, fluorine, chlorine, bromine or straight-chain or branched alkyl having up to 4 carbon atoms, $R^7$ denotes hydrogen, straight-chain or branched alkyl having up to 4 carbon atoms or the triphenylmethyl group, and A denotes an azetidinyl, piperidyl, pyrrolidinyl or morpholinyl radical bonded via the nitrogen atom, each of which is substituted by a radical of the formula

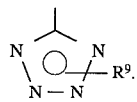

11. A substituted 2,4-imidazolidinedione or salt thereof according to claim 1, in which $R^1$ represents straight-chain or branched alkyl having up to 5 carbon atoms, $R^2$ represents cyclopropyl, cyclopentyl or cyclohexyl, or represents straight-chain or branched alkyl having up to 5 carbon atoms or benzyl, or represents a radical of the formula —$CH_2CO_2R^4$, in which $R^4$ denotes hydrogen or straight-chain or branched alkyl having up to 4 carbon atoms or represents phenyl which is optionally substituted by fluorine, chlorine, bromine or trifluoromethyl, $R^3$ represents a radical of the formula

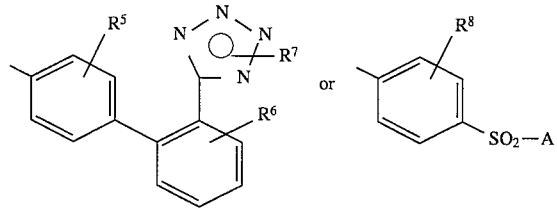

in which $R^5$, $R^6$ and $R^8$ are identical or different and denote hydrogen, fluorine, chlorine or bromine, $R^7$ denotes hydrogen, methyl, ethyl, propyl, isopropyl or the triphenylmethyl group, and A denotes an azetidinyl, piperidyl or pyrrolidinyl radical bonded via a nitrogen atom, each of which is substituted by a radical of the formula

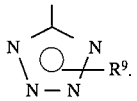

* * * * *